ically produces β-cyclodextrin from starch or partial hydrolysate thereof and produces a carbohydrate containing β-cyclodextrin as the main components, and a method for preparation thereof comprising cultivating a cyclomaltodextrin glucanotransferase producing microorganism belonging to a moderate thermophile *B. coagulans* are provided.

United States Patent [19]

Hirikoshi

[11] Patent Number: 5,019,507
[45] Date of Patent: May 28, 1991

[54] NOVEL CYCLOMALTODEXTRIN GLUCANOTRANSFERASE

[75] Inventor: Koki Hirikoshi, Tokyo, Japan

[73] Assignee: Rikagaku Kenkyusho, Wako, Japan

[21] Appl. No.: 305,631

[22] Filed: Feb. 3, 1989

[30] Foreign Application Priority Data

Feb. 4, 1988 [JP] Japan .................. 63-24478

[51] Int. Cl.$^5$ .................. C12N 9/10; C12R 1/07; C12P 19/18
[52] U.S. Cl. .................. 435/193; 435/97; 435/101; 435/252.5; 435/832; 536/103
[58] Field of Search .................. 435/101, 193, 97, 832, 435/252.5; 536/103

[56] References Cited

PUBLICATIONS

Kitahara et al., Agric. Biol. Chem., vol. 38(2), pp. 387–393 (1974).
Kitahar et al., Agric. Biol. Chem., vol. 38, p. 2413 (1974).
Nakamura et al., Agric. Biol. Chem., vol. 40, p. 753 (1976).
Biotech Abstract 88-08682 ABCHA6, "Agric. Biol. Chem.", 52, 2, pp. 1099–1103 (1988).
Biotech Abs. 88-07767 (J63068081) Oji-Corn-Starch, Mar. 1988.
Biotech Abs. 89-01127 (WO880831), Genetics-Inst, Oct. 1988.
*Chemical Abstracts*, (1982), vol. 96, p. 372, Abstract No. 138639d, "Purification and Some Properties of Cyclodextrin Glucanotransferase . . . ", Kitahata et al.
*Agric. Biol. Chem.*, (1988), vol. 52, pp. 1099–1103, "Purification and Some Properties of Cyclomaltodextrin Glucanotransferase . . . ", Yagisawa.
*Carbohydrate Research*, (1978), vol. 61, pp. 229–238, "Purification and Some Properties of Bacillus Macerans Cycloamylose . . . ", Kobayashi et al.

*Primary Examiner*—Herbert J. Lilling
*Attorney, Agent, or Firm*—Oblon, Spivak, McClelland, Maier & Neustadt

[57] ABSTRACT

A novel cyclomaltodextrin transferase (EC. 2, 4, 1, 19) which preferentially produces β-cyclodextrin from starch or partial hydrolysate thereof and produces a carbohydrate containing β-cyclodextrin as the main components, and a method for preparation thereof comprising cultivating a cyclomaltodextrin glucanotransferase producing microorganism belonging to a moderate thermophile *B. coagulans* are provided.

1 Claim, 6 Drawing Sheets

NOVEL CYCLOMALTODEXTRIN GLUCANOTRANSFERASE

BACKGROUND OF THE INVENTION

1. Field of the Invention

The present invention relates to a novel cyclomaltodextrin transferase (EC. 2, 4, 1, 19; hereinafter referred to as CGTase) which preferentially produces beta-cyclodextrin (hereinafter referred to as $\beta$-CD) from starch and a method for preparation thereof. The present invention particularly relates to a novel CGTase which is obtained by cultivation of *Bacillus coagulans* and which preferentially produces $\beta$-CD from starch or partial hydrolysates thereof to form a carbohydrate containing $\beta$-CD as main components, and a method for preparation thereof.

2. Description of the Prior Art

A CGTase is an enzyme catalyzing the following reactions: CD producing reactions producing cyclodextrins (hereinafter referred to as CDs) by acting on the $\alpha$-1,4-glucopyranoside bond of an $\alpha$-1,4-glucan such as starch, amylose, amylopectin and glycogen or partial hydrolysate thereof; coupling reactions cleaving CDs and transferring their glycosyl residues to several glycosyl accepters such as sucrose and maltooligosaccharides; and disproportionation reactions producing maltooligosaccharides with various molecular weights by intermolecular transferring reaction of various maltooligosaccharides. $\alpha$-CD (cyclohexaamylose) consisting of six glucose units, $\beta$-CD (cycloheptaamylose) consisting of seven glucose units and $\Gamma$-CD (cyclooctaamylose) consisting of eight glucose units are well-known as CDs but branched CDs branching at the 6th-position of glucose of CDs through $\alpha$-1,6-glucopyranoside bond are also manufactured.

These CDs have a character to make inclusion complexes by incorporating various organic compounds (referred to as guest compounds) into cavities thereof due to their specific structure exhibiting hydrophobic nature. As a result, CDs advantageously improve properties of the guest compounds such as stability to heat, oxygen or ultraviolet rays and solubility in water and various solvents. Thus CDs are utilized not only in the field of foods but also in the pharmaceutic, cosmetic, pesticide and various other fields.

As mentioned above, CDs are obtained as a mixture of various CDs and maltooligosaccharides by the action of CGTase on an $\alpha$-1,4-glucan such as starch or partial hydrolysate thereof as a mixture of various CDs and maltooligosaccharides but the product yield and yield ratio of the CDs varies slightly depending on the origin of the CGTase. Several microorganisms are known as sources of CGTases but microorganisms belonging to *Bacillus* known as particularly good producers of a CGTase. For example, the following microorganisms are known: B.macerans (Biochemistry, vol. 7, p 114, 1968 and Agric. Biol. Chem., vol. 38, p 387, 1974 and ibid, vol. 38, p 2413, 1974); *B.circulans* (Amylase Symposium, vol. 8. p 21, 1973); *B.mecaterium* (Agric. Biol. Chem., vol. 38, p 387, 1974 and ibid, vol. 38, p 2413, 1974); *B.stearothermophilus* (Japanese Patent No. 947335, J. Jap. Soc. Starch Sci., vol. 29, p 7, 1982); and alkaliphilic *Bacillus* sp. (Die Starke, vol. 27, p 410, 1975, Agric. Biol. Chem., vol. 40, p 935, 1976 and ibid, vol. 40, p 1785, 1976).

Aside from microorganisms belonging to *Bacillus*, *Klebsiella pneumoniae* (Arch. Microbiology, vol. 111, p 271, 1977, Carbohydr. Res., vol. 78, p 133, 1980 and ibid, vol. 78, p 147, 1980) is reported to produce a CGTase. The CGTases produced by various microorganisms are classified into $\alpha$-CD and $\beta$-CD-forming types on the basis of the initial reaction product produced from starch. *B.macerans* and *K.pneumoniae* produce $\alpha$-CD-forming type and *B.circulans*, *B.megaterium* and alkaliphilic *Bacillus* sp. produce $\beta$-CD-forming type. Further, the CDs content of a reaction product produced by a CGTase of *B.stearotheromphilus* from starch is as follows: $\beta$-CD > $\alpha$-CD > $\Gamma$-CD. However, this CGTase is properly $\alpha$-CD type because the initial reaction product of this CGTase is $\alpha$-CD (Japanese Patent No. 947335 and J. Jap. Soc. Starch Sci., vol. 29, p 13, 1982).

A CGTase of $\Gamma$-CD producing type was recently found but its $\Gamma$-CD productivity is quite low, making it inappropriate for practical use (Denpun Kagaku, vol. 33, p 137, 1986 and Japanese Patent Disclosure No. 61-274680).

Proper use of a CGTase according to purpose is advantageous since CGTases from different sources exhibit different action depending on pH and temperature, as well as different product yields and yield ratios of CDs from starch. However, a CGTase with a suitable optimum temperature and pH or better stability to temperature and pH is easier to use industrially. In general, it is preferred that the optimum temperature of an enzyme used for production of a starch sugar such as amylase be between 65° and 70° C. and that the optimum pH thereof be in the weak acid range of from 4.5 to 6.5. One reason for setting the optimum temperature at 65° to 70° C. is to prevent microorganism pollution of the reaction solution. Microorganism pollution makes it necessary to use large amounts of alkaline agents such as sodium hydroxide to compensate for pH drop of the reaction solution which results from the pollution and also requires purification by, for example, deionizing and decoloring, which makes the process expensive and difficult. Further, use of CGTases having higher optimum temperature and stable temperature is not economical because it requires more energy to maintain the temperature of the reaction vessel and inactivate the enzymes.

Moreover, when CGTases having an optimum pH in the alkaline range are used, an isomeric reaction occurring simultaneously with the enzyme reaction and colorization reduce the product yield and make the purification operation complicated. Therefore use of such a CGTase is not economical.

As described above, CGTases useful for industrial processes have to exhibit not only high yield of CDs from starch but also suitable optimum temperature, optimum pH and temperature stability for practical use.

SUMMARY OF THE INVENTION

An object of the present invention is to provide a $\beta$-CD type CGTase capable of producing CDs from starch cheaply and with high productivity.

Another object of the present invention is to provide a $\beta$-CD type CGTase which has an optimum temperature of about 65° C., at which pollution with microorganisms during reaction can be prevented, which can be inactivated at about 80° C. and which has an optimum pH in the weak acid range.

A further object of the present invention is to provide a process for preparation of a novel CGTase having the above properties.

Other objects of the present invention will be apparent from the following detailed explanation of the invention.

The aforementioned objects of the invention can be accomplished by providing a CGTase having the following physical properties:

(a) Action: Cuts α-1,4-glucopyranoside bonds of an α-1,4-glucan such as starch and glycogen, or partial hydrolysate thereof and transfers it to form cyclodextrins and produces β-cyclodextrin as the initial reaction product of its transferring;

(b) Substrate specificity: Reacts with a maltooligosaccharide having α-1,4-glucopyranosidic linkages with a chain length not less than that of maltotriose to form various maltooligosaccharides with various molecular weight and cyclodextrins by intermolecular disproportionating reaction between substrates;

(c) Optimum pH: About 6.5

(d) Stable pH: Stable at pH 6 to 9 at 40° C. for 2 hours;

(e) Optimum temperature: About 65° C.;

(f) Inactivation condition: Completely inactivated by treatment at pH of 4.5 and 11.5 at a temperature of 40° C. for 2 hours and by treatment at pH of 6 at 75° C. for 15 minutes;

(g) Heat stability: Stable up to 50° C. under the condition of pH 6 for 15 minutes and residual activity at 60° C. and 70° C. is 95% and 20% respectively under the same condition;

(h) Inhibition: Inhibited by mercury (II) or copper (II);

(i) Activation and stabilization: Stabilized by calcium;

(j) Molecular weight (SDS-polyacrylamide gel electrophoresis): 36,000±1,000;

(k) Isoelectric point (chromatofocusing): 4.8±0.1.

DETAILED DESCRIPTION OF THE PREFERRED EMBODIMENTS

The CGTase of the present invention can be produced by cultivating a CGTase producing microorganism belonging to *Bacillus coagulans*, which is a moderate thermophile obtained from soil, and collecting the CGTase produced extracellularly into the culture fluid.

The CGTase producing microorganism used in the present invention which has been discovered and isolated from soil by the inventors of this invention was identified as *Bacillus coagulans* from the facts that it is aerobic, Gram-positive, spore-forming rods, motile and peritrichous flagella. Taxonomical studies of the isolated strain was performed with reference to Bergey's Manual of Systematic Bacteriology, vol. 1 published by Williams and Wilkius, Baltimore/London and The Genus *Bacillus*, published by the U.S. Department of Argiculture. Further the isolated strain has been identified as *Bacillus coagulans* from the fact that it does not grow at 65° C. but grows at a temperature of from 30° to 60° C. and in the presence of 0.02% of sodium azide, does not produce ammonia from urea, and produces dihydroxyacetone.

Japanese Patent No. 947335 discloses that a CGTase producing microorganism (FERM P-2219) belonging to *B.stearothermophilus* grows at 60° C. and does not grow at 65° C. However, the isolated strain (YH-1306) of the present invention grows in the presence of 3% sodium chloride and cannot utilize inorganic nitrogen compounds, the shape of the sporangium is different from that of FERM P-2219 and it can be concluded that the isolated bacterial strain of the present invention is a novel microorganism producing CGTase. Further, as described below, the enzymatic properties and substrate specificity of the CGTase produced by the strain (YH-1306) are different from those described in Japanese Patent No. 947335 and therefore the strain (YH-1306) is considered to be novel. The isolated strain (YH-1306) does not grow under alkaliphilic conditions and does not assimilate citric acid and is therefore obviously different from *B.megaterium* and *B.circulans*. In conclusion, the strain (YH-1306) of the present invention is identified as a microorganism belonging to *B.coagulans*. Taxonomical properties of the strain (YH-1306) are listed in Table 1 below.

TABLE 1

| Taxonomical properties of YH-1306 | |
|---|---|
| 1. Morphological characteristics | |
| Gram-positive *Bacillus* (0.7 to 1.0 micron × 2 to 4 microns) having motility and peritrichous flagella. The sporangium is not expanded or only slightly expanded and the spores (0.9 to 1.0 micron × 1.5 to 2.0 microns) are ellipsoidal and located at the end or near the end of the sporangium. | |
| 2. Growth in various cultures | |
| Nutrient agar plate culture: Forms yellowish round colonies. Surface elevations are capitate. | |
| Nutrient agar slant culture: Grows in a spreading form. | |
| Nutrient gelatin agar stab culture: Gelatin is not liquidized. | |
| Litmus milk: Produces acid without coagulation. | |
| Broth liquid culture | |
| 0.5% NaCl: Grows, with sediment | |
| 3% NaCl: Grows slightly | |
| 5% NaCl: Does not grow | |
| 0.02% azide: Grows slightly | |
| 3. Growth pH and temperature | |
| Growth pH: 5.8 to 7.5 (Optimum pH: 6.5 to 7.0) | |
| Growth temperature: 30 to 60° C. | |
| (Optimum temperature: 45 to 50° C.) | |
| 4. Biochemical properties | |
| Reduction of nitrate | − |
| Denitrification | − |
| Methylred test | − |
| VP test | − |
| Production of acid in VP broth | + |
| Production of ammonia from urea | − |
| Production of indole | − |
| Production of hydrogen sulfide | − |
| Production of dihydroxyacetone | + |
| Decomposition of tyrosine | − |
| Assimilation of citric acid | − |
| Decomposition of casein | + |
| Hydrolyzation of starch | + |
| Liquefaction of gelatin | + |
| Utilization of inorganic nitrogen compounds | − |
| Production of pigment(s): Yellow pigment is produced | |
| Urease test | + |
| Oxidase test | − |
| Catalase test | + |

TABLE 1-continued

| Taxonomical properties of YH-1306 | |
|---|---|
| Production of gas from glucose | − |
| Production of acid from sugar | |
| Glucose | + |
| Arabinose | + |
| Lactic acid | − |
| Mannitol | + |
| 5. Other properties | |
| OF test: Oxidative | |
| Behavior in oxygen: Aerobic (grows only slightly in an anaerobic condition) | |
| GC content: 46 ± 1% (HPLC) | |
| Resistivity to lysozyme | − |

+ : positive or grows well
− : negative or does not grow

The strain (YH-1306) used in the present invention was deposited with the Fermentation Research Institute (FRI) in accordance with the Budapest Treaty under the accession number of FERM BP-2258.

The novel CGTase of the present invention will now be explained in detail. The CGTase producing microorganism belonging to *B.coagulans* is inoculated to a culture whose pH is regulated to 5.8 to 7.5, preferably from 6.5 to 7.0, and then the inoculated culture is aerobically cultivated at a temperature between 30° and 60° C., preferably between 45° and 50° C. for from 30 to 80 hours to produce and accumulate the CGTase in the cultivation fluid as an extracelluar enzyme.

Various materials which are known and cheaply available can be applied to the culture used in the present invention. Examples of nitrogen sources include corn steep liquor, polypeptone, soybean meal, bran, meat extract, yeast extract and amino acid solution. Examples of carbon sources include corn syrup, maltose, various starches, soluble starch, liquefied starch, dextrin and pullulan.

In addition to the nitrogen and carbon sources, various salts such as inorganic salts (for example magnesium salt, potassium salt, phosphate, ferric salt) and various vitamins may be optionally added to the culture.

An example of a culture suitable for the above cultivation is a liquid culture containing 5% corn steep liquor, 0.1% $K_2HPO_4$, 0.02% $MgSO_4.7H_2O$, and 0.005% $CaCl_2.2H_2O$.

The CGTase producing microorganism (FERM BP-2258) used in the present invention produces an extracellular enzyme. The extracellular enzyme accumulated in the culture supernatant is subjected to centrifugal separation to remove microbial cells and obtain a crude enzyme. Use of the resulting crude enzyme without purification is economical. However, the crude enzyme may be purified and this purification can be conducted by, for example, salting out with ammonium sulfate, solvent precipitation with ethanol, acetone or isopropanol, ultrafiltration or general enzyme purification using an ion exchange resin.

A preferred example of a method for preparation of the pure CGTase of the present invention will be explained.

A moderate thermophile *Bacillus coagulans* (YH-1306) is inoculated to a medium containing 5% (w/v) corn steep liquor, 0.1% $K_2PO_4$, 0.02% $MgSO_4.7H_2O$ and 0.005% $CaCl_2.2H_2O$ and then aerobically cultivated at 45° C. for 72 hours under the following conditions: aeration rate of 1 v.v.m. and agitation at 250 r.p.m.

The resulting cultivation solution is subjected to a continuous centrifugal separation at 10,000 r.p.m. at a temperature of 4° C. to remove bacterial cells and obtain a supernatant (crude enzyme solution). Then solid ammonium sulfate is added to the crude enzyme solution to saturate up to about 20%. The solution is passed through a corn starch layer to adsorb the enzyme from the solution and the enzyme is then extracted with an excess volume of 40 mM disodium hydrogen phosphate solution. The resulting extract solution is concentrated by use of an ultrafiltration membrane (average fraction molecular weight: 10,000) and then the concentrated solution is subjected to dialysis against a 10 mM acetate buffer solution (pH 6.0) containing 1 mM $CaCl_2$ at 4° C. overnight. The precipitates formed during the dialysis are removed by centrifugation. The resulting supernatant is adsorbed on a DEAE-Toyopearl 650M column equilibrated with, for example the 10 mM acetate buffer solution and the enzyme is eluted with a similar buffer solution containing 0 to 0.7M NaCl by the linear gradient method. The eluted active fractions are collected and concentrated using the above-mentioned ultrafiltration membrane. Then the concentrated fractions are loaded onto a Sephacryl S-200 column equilibrated with the same buffer solution containing 0.1M NaCl and subjected to eluation with the buffer solution.

The eluted active fractions are collected and concentrated by the above-mentioned ultrafiltration membrane. The concentrated fractions are subjected to high performance liquid chromatography using a Shodex WS-2003 column to collect active fractions. The resulting purified enzyme is analyzed by polyacrylamide gel disc electrophoresis (PAGE, gel concentration: 7.5%) and the analysis shows that the purified enzyme is homogeneous and the yield of enzyme activity by this purification is about 25%.

The β-CD-forming activity can be determined by the method of Kaneko et al (J. Jpm. Soc. Starch Sci., vol. 34, p 45-48, 1987) as follows. The reaction mixture containing 1.0 ml of 4% (w/v) soluble starch solution in 0.1M acetate buffer solution (pH 6.0) and 0.1 ml of an enzyme solution is incubated at 60° C. for 20 minutes, whereafter the reaction is stopped by addition of 3.5 ml of 30 mM NaOH solution. Then 0.5 ml of 0.02% (w/v) phenolphthalein in 5 mM $Na_2CO_3$ solution is added to the reaction mixture and the color of the resulting solution after keeping for about 15 minutes at room temperature is measured by a photoelectric colorimeter (Klett-Summerson type) using a filter No.54 (550 nm) with 1.0 ml of 0.5 mg/ml β-CD solution, as a standard, which is simultaneously treated with the phenolphthalein solution. A unit of the enzyme activity is defined as follows: amount of the enzyme required to form 1 mg β-CD per 1 minute under the condition described above.

The physical and enzymological properties of the CGTase obtained by the method of the present invention are compared with those of CGTases obtained from known bacteria and shown in Table 2.

TABLE 2

| | Comparison of enzymological properties | | |
|---|---|---|---|
| Properties | Present Invention | ABC-38 | ABC-40 |
| Origin | *B. coagulans* | *B. megaterium* | alkalophilic |

TABLE 2-continued

Comparison of enzymological properties

| | | | Bacillus acidic CGTase (A.C.): 4.5 neutral CGTase (N.C.): 7 | |
|---|---|---|---|---|
| Optimum pH | 6.5 | 5 to 7.5 peak at 5.5 shoulder at 7.5 | | |
| Optimum temp. | 65° C. | 55° C. | A.C.: 45° C. N.C.: 50° C. | |
| Temp. Stability | 15 minutes treatment | 10 minutes treatment | 30 minutes treatment | |
| (residual activity) | 60° C.  93%<br>65° C.  55%<br>70° C.  20%<br>75° C.   0% | 55° C.  100%<br>60° C.   25%<br>65° C.    2% | 40° C.<br>50° C.<br>60° C.<br>70° C. | A.C.<br>100%<br>25%<br>0%<br>0% | N.C.<br>100%<br>100%<br>100%<br>95% |
| pH Stability | 40° C., 2 hrs treatment | 40° C., 2 hrs treatment | 60° C., 30 mins treatment | |
| (residual activity) | pH 4.5    0%<br>5.0   65%<br>6-9  100%<br>10    90% | pH 5.7       7%<br>6.0  30-42%<br>7-10   100%<br>11   67-75% | pH 5<br>6<br>7-9<br>10 | A.C.<br>5%<br>90%<br>100%<br>10% | N.C.<br>20%<br>100%<br>100%<br>100% |
| Molecular Weight | 36,000 ± 1000 | 66,000 | 85,000–88,000 | |
| Isoelectric point | 4.8 ± 0.1 | fraction<br>1: 6.07<br>2: 6.80 | 5.4 | |
| Initial product from starch | β-CD | β-CD | β-CD | |
| Final CDs component | β-CD>α-CD>Γ-CD | β-CD>α-CD>Γ-CD | β-CD>α-CD>Γ-CD | |

| Properties | JP Patent No. 947335 | ABC-38 |
|---|---|---|
| Origin | B. stearothermophilus | B. macerans (IFO 3490) |
| Optimum pH | 3.5 to 8.5 peaks at 5.5 and 7.5 | 5.2 to 5.7 |
| Optimum temp. | 75° C. | 55° C. |
| Temp. Stability | 15 minutes treatment | 10 minutes treatment |
| (residual activity) | 60° C. 100%<br>70° C.  90%<br>75° C.  55%<br>80° C.  10% | 55° C. 100%<br>60° C.  95%<br>65° C.  70%<br>70° C.  10% |
| pH Stability | 40° C., 2 hrs treatment | 40° C., 2 hrs treatment |
| (residual activity) | pH 4.5   10%<br>5.0   80%<br>6-8  100% | pH 5     0%<br>6    70%<br>7    75%<br>8    95%<br>9-10 100%<br>11   90% |
| Molecular Weight | 70,000 ± 40,000 | 65,000 |
| Isoelectric point | 4.45 | 4.6 |
| Initial product from starch | α-CD | α-CD |
| Final CDs component | β-CD>α-CD>Γ-CD | β-CD>α-CD>Γ-CD |

ABC-38: Agric. Biol. Chem., vol. 38, 387, 1974 and ibid, vol. 38, 2413, 1974
ABC-40: Agric. Biol. Chem., vol. 40, 935, 1976 and ibid, vol. 40, 1785, 1976

As shown in Table 2, the CGTase of the present invention is different from CGTases of B.stearothermophilus and B.macerans in the initial product from starch. Further the CGTase of the present invention is different from the enzyme of alkalophilic Bacillus sp. in the CDs composition of the final product.

Although the initial product and the CDs composition of the final product of the CGTase of the present invention are the same as those of the CGTase of B.mecaterium, they are different in profiles of pH and temperature on activity and stability. From the industrial viewpoint, use of the enzyme of B.macerans is preferred for production of α-CD and use of an enzyme of alkalophilic Bacillus sp. is preferred for production of β-CD, but both of these enzymes have disadvantages in optimum temperature and temperature stability.

Use of CGTases of B.megaterium and B.stearothermophilus is suitable for production of ò, β and Γ-CD in good proportion. However, the CGTase of B.megaterium has disadvantages in optimum temperature and temperature stability and pollution of the reaction mixture with bacteria cannot be sufficiently prevented. The CGTase of B.stearothermophilus has high optimum temperature and exhibits superior temperature stability.

The optimum temperature and temperature stability of an enzyme are generally measured in the absence of a substrate or at a low substrate concentration but reaction is practically conducted using a high concentration of substrate such as 10 to 20% (w/v) from an economical viewpoint. In the solution containing a substrate in a high concentration, the enzyme is generally stabilized by the protecting action of the substrate. Similarly, the CGTase is stabilized in a substrate solution and exhibits higher temperature stability than in a solution without the substrate. CDs obtained by reaction of a CGTase with starch are generally purified by crystalization, membrane separation or chromatography using an ion exchange resin or a gel filtration resin but after reaction of the CGTase, a fair amount of high molecular weight dextrins and maltooligosaccharides remain in the reaction solution due to the substrate specificity of the CGTase. These remaining components actually make impossible operations such as deionization and filtration and therefore the reaction solution is subjected to action of amylolytic enzymes such as $\alpha$-amylase, $\beta$-amylase, glucoamylase and $\alpha$-1,6-glucosidase to hydrolyze and decompose the high molecular weight dextrins and maltooligosaccharides and reduce the viscosity of the reaction solution. When the CGTase used to the CDs production reaction is still active after the reaction, as mentioned above, the produced CDs are hydrolyzed by coupling and disproportionating actions of the CGTase during the saccharification step to reduce the viscosity of the solution. For the above reasons, the CGTase has to be completely inactivated using before various amylolytic enzymes for the re-saccharification of the oligosaccharides and dextrins aside from CDs. Use of acids and alkaline agents is not economical for the following reasons: Undesirable side reactions such as hydrolysis and isomerization occur and much energy and labor are necessary for purification such as deionization and decoloration because pH should be re-adjusted with alkaline agents or acids at the optimum pH of the enzyme used for re-saccharification prior to the re-saccharification. Thus heat inactivation is generally used for inactivation of CGTases. However, the heat inactivation is not economical for inactivation of the CGTase of *B.Stearothermophilus* because it has high temperature stability. Under the circumstances, use of the CGTase of the present invention is quite economical because it has not only an optimum temperature suitable for prevention of microbial pollution of a reaction vessel and temperature stability suitable for heat inactivation but also an optimum pH similar to those of various amylases used for re-saccharification of dextrins and oligosaccharides.

According to a method of the present invention, the CGTase useful for preparation of CDs from starch can cheaply be provided in large amounts. Further carbohydrates containing $\alpha$, $\beta$ and $\Gamma$-CDs in good proportion can be prepared by the CGTase in large scale.

EXAMPLES

The novel CGTase of the present invention and a method for preparation thereof will now be explained referring to following Examples. However, the scope of the present invention is not limited by the Examples.

EXAMPLE 1

A moderate thermophile *Bacillus* YH-1306 (FERM BP-2258) strain was inoculated to 300 ml of a medium (pH 6.8) containing soluble starch 1%, polypeptone 1.5%, yeast extract 0.5%, $K_2HPO_4$ 0.1%, $MgSO_4.7H_2O$ 0.02% and $CaCl_2.2H_2O$ in a two liters conical flask with flutings and cultivated at 45° C., 200 r.p.m. for 20 hours to form a seed solution. The resulting seed solution 290 ml was added to 15 liters of a medium having the same composition as the medium used above in a 30 liters jar fermenter and aerobically cultivated at 45° C. and at an aeration rate of 1.5 v.v.m. for 48 hours under agitation at 250 r.p.m.. After cultivation, bacterial cells were removed by continuous centrifugation (12,000 g, 4° C.) and the resulting supernatant was subjected to concentration by use of an ultrafiltration (average molecular weight: 10,000) to make the concentration about ten times as that of the supernatant and obtain about 1.5 liters of a crude enzyme solution having 180 units/ml of the CGTase.

Then solid ammonium sulfate is added to the crude enzyme solution to saturate up to 20%. The solution is passed through a corn starch layer to adsorb the enzyme from the solution and the enzyme is then extracted with an excess volume of 40 mM disodium hydrogen phosphate solution. The resulting extract solution is concentrated by use of an ultrafiltration membrane (average fraction molecular weight: 10,000) and then the concentrated solution is subjected to dialysis against a 10 mM acetate buffer solution (pH 6.0) containing 1 mM $CaCl_2$ at 4° C. overnight. The precipitates formed during the dialysis are removed by centrifugation. The resulting supernatant is adsorbed on a DEAE-Toyopearl 650M column equilibrated with the 10 mM acetate buffer solution and the enzyme is eluted with a similar buffer solution containing 0 to 0.7M NaCl by the linear gradient method. The eluted active fractions are collected and concentrated using the above-mentioned ultrafiltration membrane.

The resulting crude enzyme solution was loaded onto a Sephacryl S-200 column equilibrated with a 10 mM acetate buffer solution (pH 6.0) containing 0.1M sodium chloride and eluation was conducted with the same buffer solution. Eluded active fractions were collected and concentrated using the ultrafiltration membrane used above. The concentrated solution was subjected to high performance liquid chromatography using a Shodex WS-2003 column to collect active fractions. The resulting purified enzyme is analyzed by polyacrylamide gel disc electrophoresis (gel concentration: 7.5%) and the analysis showed that the purified enzyme had single component and the active yield was about 25%.

EXAMPLE 2

Figure 1:
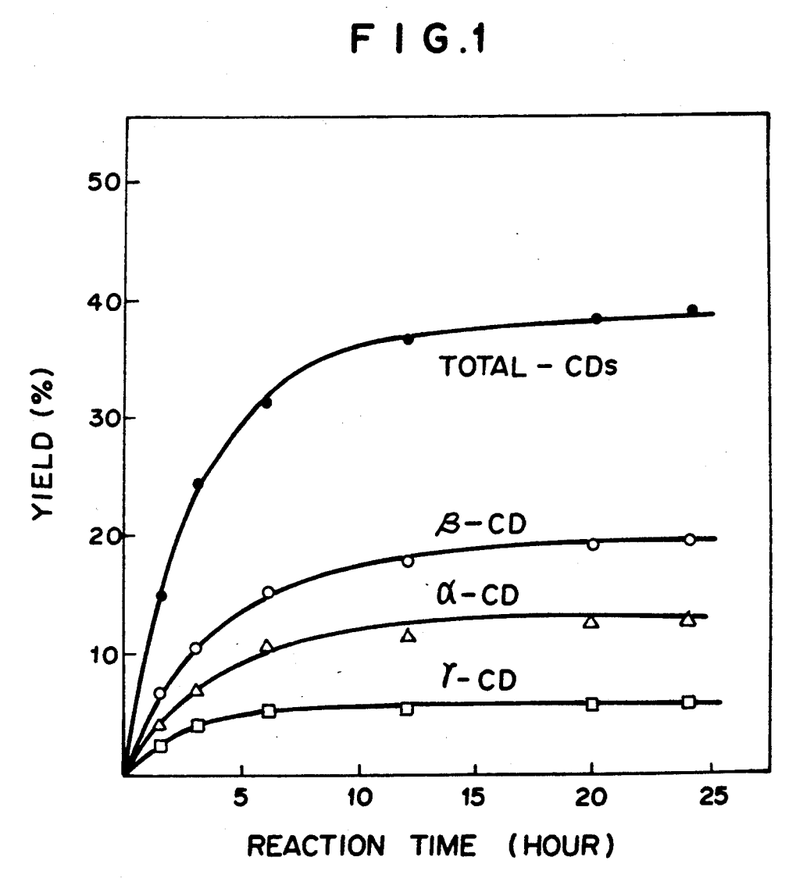
FIG. 1 shows time-course change of α, β, Γ and total CD when the CGTase of the present invention is used.

(a) 100 ml of 13% (w/v) potato starch suspension (pH 6.5) containing 3 mM $CaCl_2.2H_2O$ was liquefied using a bacterial liquefying type $\alpha$-amylase (manufactured by Daiwa Kasei K. K., Chrystase L-1) at 90° to 92° C. and immediately heated at 125° C. for 30 minutes to obtain a starch liquefied solution with 1.2 of D.E. (Dextrose Equivalent: ratio of total solid to direct reducing sugar). Then the purified CGTase obtained in Example 1 was added to the starch liquefied solution in an amount of three units per one gram of the starch liquefied solution and reacted at 70° C. and pH 6.5. This reaction mixture was sampled time-coarsely and CDs in the sampled reaction mixture were measured by high performance liquid chromatography (HPLC) using a HPX-42A column manufactured by Bio-Rad Lab.. Results are shown in FIG. 1.

(b) Specificity 55 mg of an oligosaccharide (maltose, maltotriose or maltotetraose) and 1 mM $CaCl_2.2H_2O$ was dissolved in water 1.0 ml. To the resulting solution, five units of the purified CGTase of the present invention was added and the reaction was conducted at 65° C. for 24 hours. The obtained reaction mixture was subjected to measurement by HLPC and results are listed in Table 3.

TABLE 3

Action on various oligosaccharides

Reaction products (%)

| Sub | $G_1$ | $G_2$ | $G_3$ | $G_4$ | $G_5$ | $G_6$ | others | α-CD | β-CD | Γ-CD |
|-----|-----|-----|-----|-----|-----|-----|--------|------|------|------|
| $G_2$ | 0.3 | 99.6 | 0.1 | ND | ND | ND | ND | ND | ND | ND |
| $G_3$ | 16.9 | 20.4 | 16.8 | 12.9 | 9.8 | 6.7 | 12.8 | 1.3 | 1.9 | 0.5 |
| $G_4$ | 9.0 | 15.2 | 14.4 | 13.0 | 10.7 | 11.6 | 19.7 | 2.6 | 3.0 | 0.8 |

Sub: substrate, $G_1$: glucose $G_2$: maltose, $G_3$: maltotriose, $G_4$: maltotetraose, $G_5$: maltopentaose, $G_6$: maltohexaose, ND: not detected

TABLE 4

Effect of metal salts on enzyme activity

| Metal salt | Relative activity | Metal salt | Relative activity |
|------------|-------------------|------------|-------------------|
| control | 100 | $Cu^{2+}$ | 36.0 |
| $Mn^{2+}$ | 79.3 | $Zn^{2+}$ | 62.6 |
| $Pb^{2+}$ | 91.8 | $Co^{2+}$ | 75.9 |
| $Mg^{2+}$ | 80.3 | $Hg^{2+}$ | 9.9 |
| $Ni^{2+}$ | 93.6 | $Fe^{2+}$ | 92.6 |
| $Cd^{2+}$ | 94.8 | $Fe^{3+}$ | 98.8 |

(c) Optimum pH

Figure 2:
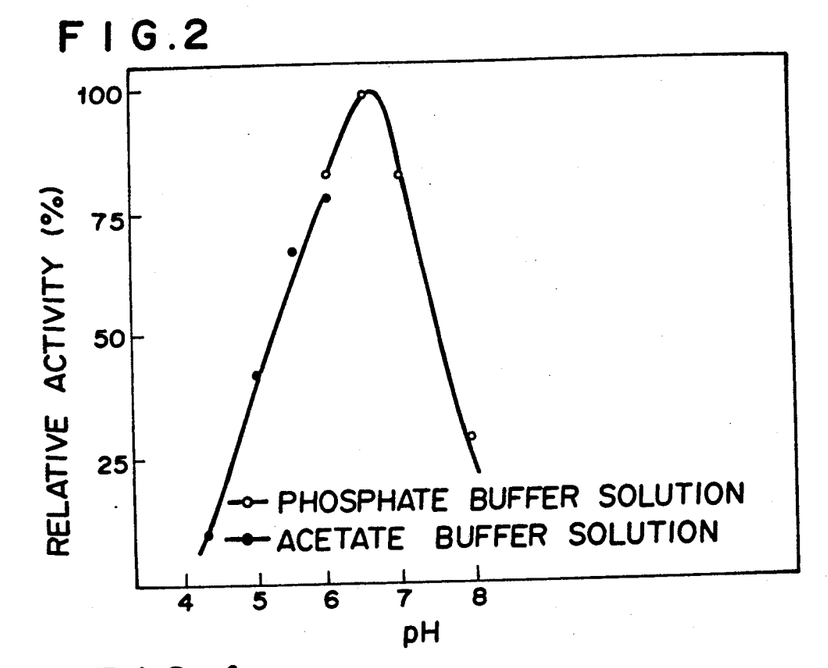
FIGS. 2 and 4 respectively show the pH effect and temperature effect on the CGTase activity.

The purified CGTase of the present invention was subjected to dialysis with 1 mM EDTA solution overnight and then with water overnight. The resulting CGTase solution (0.1 ml) deluted suitably with deionized water was mixed with 1 ml of 4% (w/v) soluble starch in 0.1M acetic acid buffer solutions (pH 4.2, 5.0, 5.5 and 6.0) or 0.1M phosphate buffer solutions (pH 6.0, 6.5. 7.0 and 8.0) and the activity of the CGTase was measured as mentioned above. The relative activity at pH 6.5 was made 100% and the pH dependence of the relative activity of the CGTase is shown in FIG. 2.

(d) Stable pH

Figure 3:
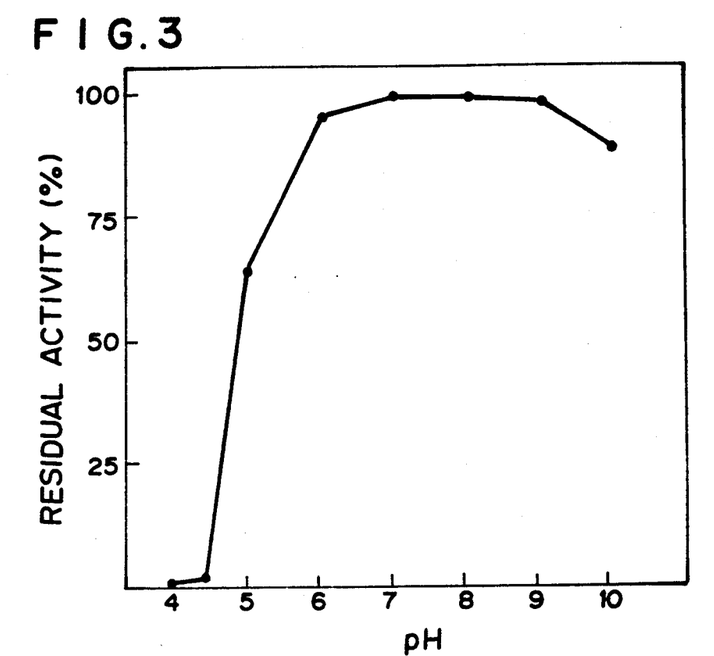
FIGS. 3 and 5 show the profiles of pH- and thermal-stabilities of the enzyme.

The dialyzed CGTase of the present invention obtained by the same procedures as those of (c) was heat treated at 40° C. for 2 hours at various pH values (4 to 10). Then the residual activity of the CGTase was measured. The activity before heating at pH 6.5 was made 100% and the pH dependence of the residual activity is shown in FIG. 3. In the above procedures, following buffer solutions were used: acetate buffer solutions (pH 4 to 6), phosphate buffer solutions (6 to 8) and glycine-NaOH-NaCl buffer solutions (pH 9 and 10).

(e) Optimum temperature for action

Figure 4:
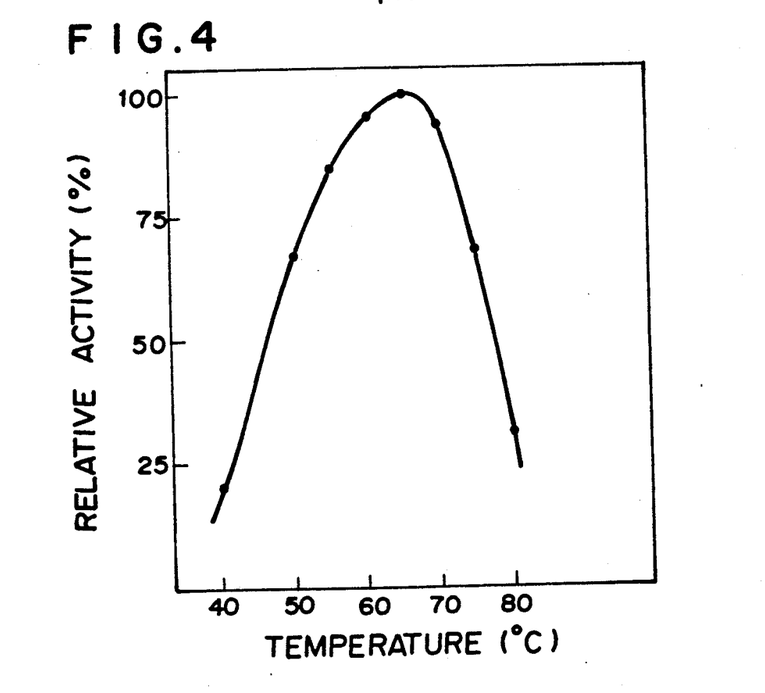

The activity of the dialyzed CGTase of the present invention obtained by the same procedures as those of (c) above was measured at various temperatures. The temperature dependence of the relative activity of the CGTase (relative activity at 65° C.: 100%) is shown in FIG. 4.

(f) Inactivation and (g) temperature stability

Figure 5:
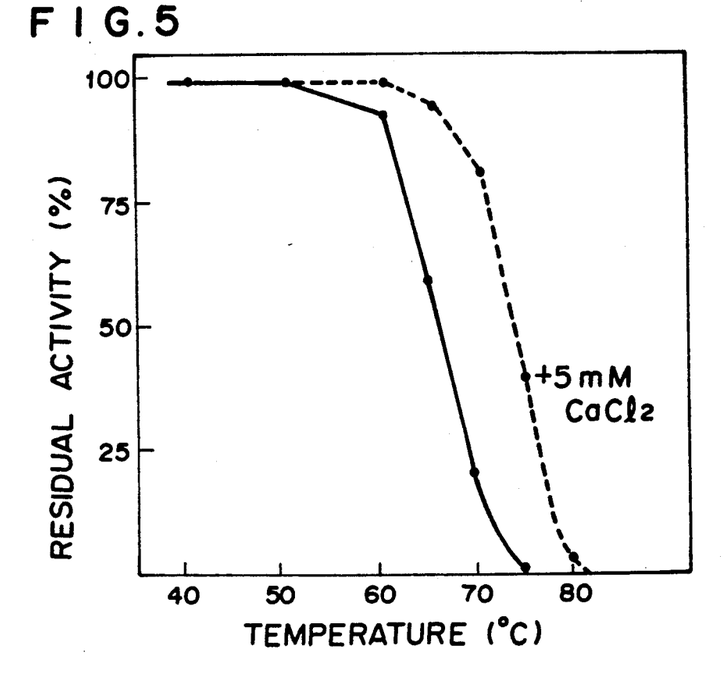

The dialyzed CGTase of the present invention obtained by the same procedures as those of (c) was treated at various temperatures (40° to 80° C.) for 15 minutes in the presence or in the absence of 5 mM $CaCl_2.2H_2O$ and then the residual activity was measured. Results are shown in FIG. 5.

(h) Inhibition

A chloride form of various metals was added to a solution containing the dialyzed CGTase of the present invention obtained by the same procedures as those of (c) to make the concentration thereof 1 mM (mercury: 0.1 mM) and then activity of the CGTase was measured. Results are shown in Table 4 as the relative activity (the relative activity of the CGTase in the absence of metal was made 100%).

(i) Stabilization

Figure 6:
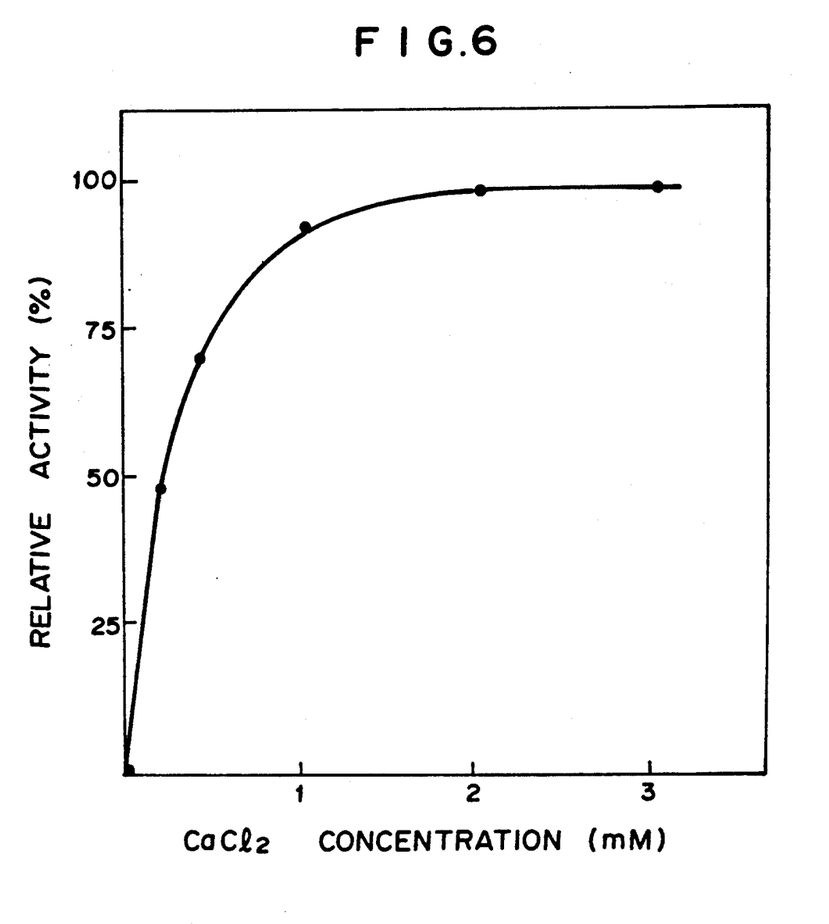
FIG. 6 shows the effect of $Ca^{2+}$ concentration on the thermal stability of the CGTase of the present invention.

Various $CaCl_2$ solutions (Ca $Cl_2$ concentration: 0 to 3 mM) were added to solutions of the dialyzed CGTase of the present invention obtained by the same procedures as those of (c) and maintained at 75° for 15 minutes. Then the residual activity of the CGTase was measured and shown in FIG. 6 as the relative activity (the relative activity in the presence of 3 mM $CaCl_2$ was made 100%).

(j) Molecular weight

Figure 7:
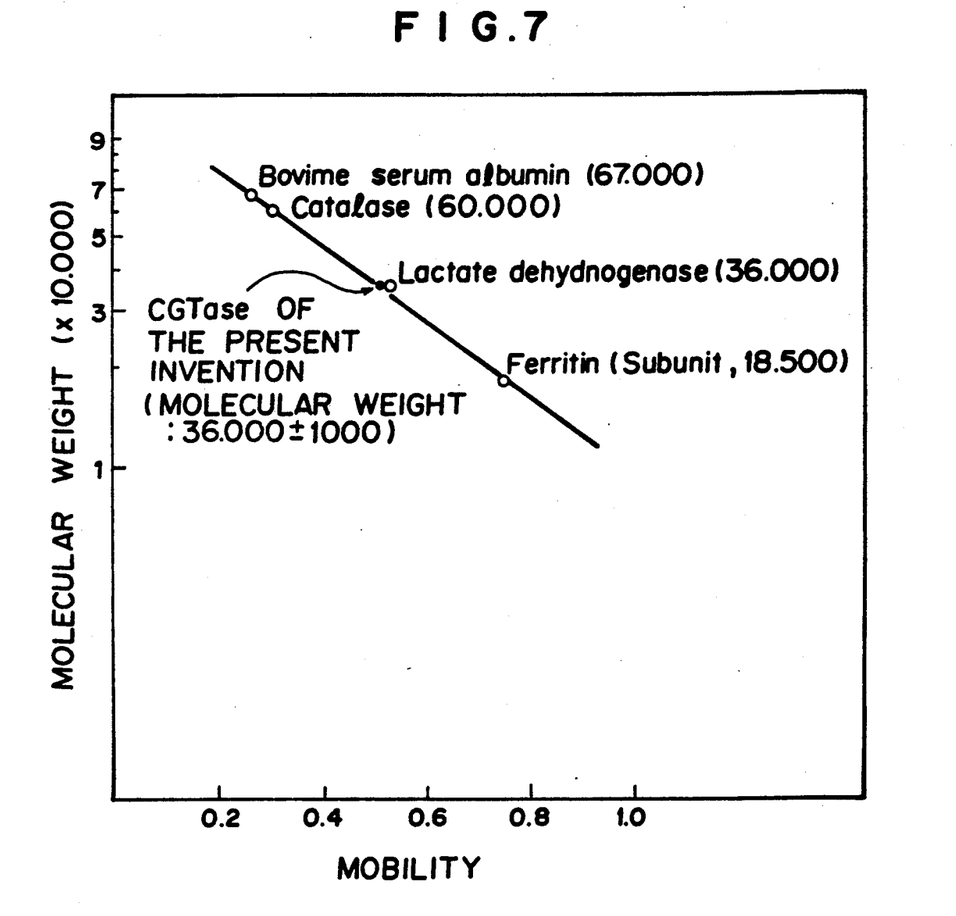
FIG. 7 shows the calculation of molecular weight of the CGTase of the present invention by SDS-PAGE.
Figure 8:
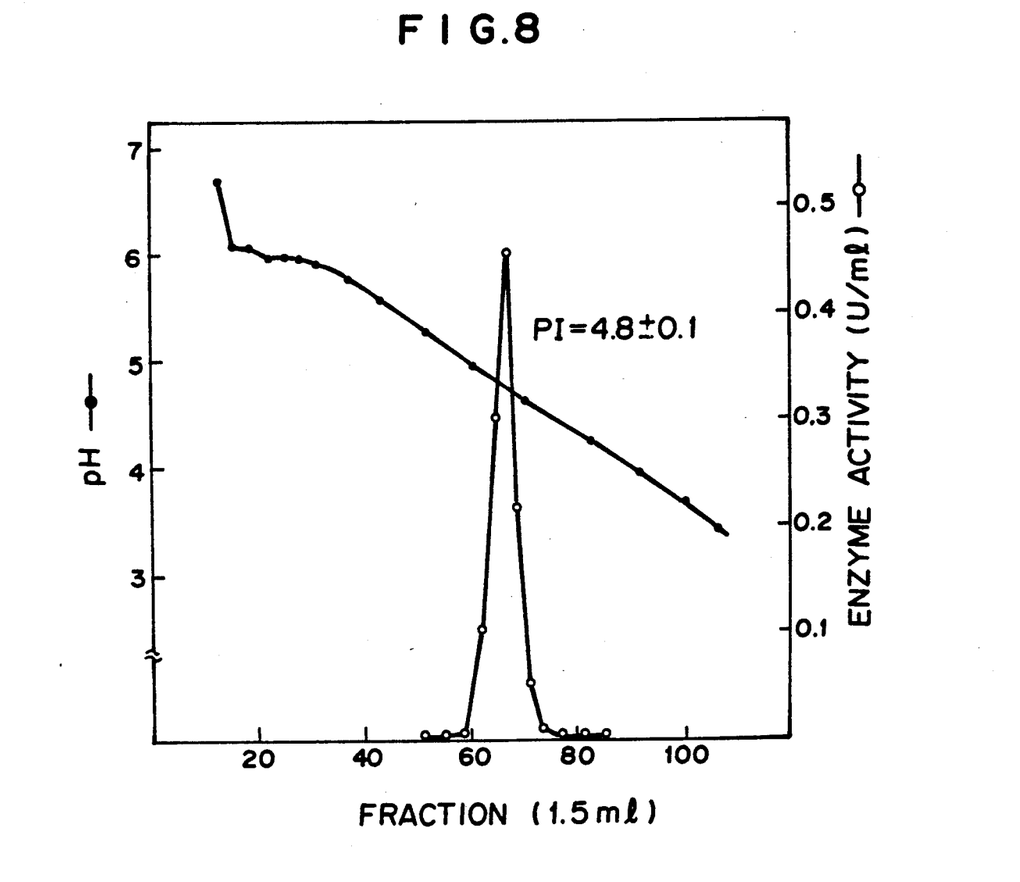
FIG. 8 is a figure showing the isoelectric point of the CGTase of the present invention to be 4.8±0.1.

The molecular weight of the CGTase of the present invention was measured by SDS-polyacrylamide gel electrophoresis (SDS-PAGE) described in K. Weber and M. Osborn, J. Biol. Chem., vol. 244, p 4406, 1969 (FIG. 7). The molecular weight of the present invention was 36,000±1,000.

(k) Isoelectric point

The isoelectric point of the CGTase of the present invention was measured by the chromatofocusing method using PBE94 gel and Polybuffer 74 manufactured by Pharmacia and was 4.8±0.1.

As described above, according to the present invention, the CGTase which has an optimum temperature of the enzyme reaction at about 65° C., which is completely inactivated at about 80° C. and which has an optimum pH similar to those of various amylolytic enzymes used for re-saccharification after CDs producing reaction is provided.

The CGTase produces maltooligosaccharides containing β-CD as main components together with an appropriate amount of α-CD and Γ-CD from starch. Further the method for preparation of CDs using the CGTase of the present invention is economical since no agent is required for the method, additional treatment such as deionization can be simplified and heat energy can be saved.

Thus the present invention makes possible to produce CDs cheaply in large scale and the present invention has industrial significance.

What we claim is:

1. A cyclomaltodextrin glucanotransferase having the following physical properties:
   (a) Action: Cuts α-1,4-glucopyranoside bonds of an α-1,4-glucan such as starch and glycogen, or partial hydrolysate thereof and transfers it to form cyclodextrins and produces β-cylsodextrin as the initial reaction product of CDs-formation reaction;

(b) Substrate specificity: Reacts with a maltooligosaccharide having α-1,4-glucopyranosidic linkages with a chain length less than that of maltotriose to form various maltooligosaccharides with various molecular weight and cyclodextrins by intermolecular coupling and disproportionating reactions between substrates;

(c) Optimum pH: About 6.5

(d) Stable pH: Stable at pH 6 to 9 at 40° C. for 2 hours;

(e) Optimum temperature: About 65° C.;

(f) Inactivation condition: Completely inactivated by treatment at pH of 4.5 and 11.5 at a temperature of 40° C. for 2 hours and by treatment at pH of 6 at 75° C. for 15 minutes;

(g) Heat stability: Stable up to 50° C. under the condition of pH 6 for 15 minutes and residual activity at 60° C. and 70° C. is 95% and 20% respectively under the same condition;

(h) Inhibition: Inhibited by mercury (II) or copper (II);

(i) Activation and stabilization: Stabilized by calcium;

(j) Molecular weight (SDS-polyacrylamide gel electrophoresis): 36,000±1,000;

(k) Isoelectric point (chromatofocusing): 4.8±0.1.

* * * * *

UNITED STATES PATENT AND TRADEMARK OFFICE
CERTIFICATE OF CORRECTION

PATENT NO. : 5,019,507

DATED : May 28, 1991

INVENTOR(S) : Koki Hirikoshi

It is certified that error appears in the above-identified patent and that said Letters Patent is hereby corrected as shown below:

TITLE PAGE: Item [75]

The inventor's name is incorrect, should be, --Koki Horikoshi--

Signed and Sealed this

Fifteenth Day of December, 1992

*Attest:*

DOUGLAS B. COMER

*Attesting Officer*      *Acting Commissioner of Patents and Trademarks*